United States Patent [19]
Okamoto et al.

[11] Patent Number: 5,856,458
[45] Date of Patent: Jan. 5, 1999

[54] OLIGONUCLEOTIDE PRIMERS, AND THEIR APPLICATION FOR HIGH-FIDELITY DETECTION OF NON-A, NON-B HEPATITIS VIRUS

[75] Inventors: Hiroaki Okamoto; Tetsuo Nakamura, both of Tokyo, Japan

[73] Assignee: Immuno Japan Inc., Tokyo, Japan

[21] Appl. No.: 470,426

[22] Filed: Jun. 6, 1995

Related U.S. Application Data

[62] Division of Ser. No. 712,875, Jun. 11, 1991.

[30] Foreign Application Priority Data

Jun. 12, 1990 [JP] Japan .................................. 2-153402

[51] Int. Cl.⁶ ............................ C07H 21/02; C07H 21/04
[52] U.S. Cl. ....................................... 536/24.3; 536/24.33
[58] Field of Search ................................. 536/23.1, 23.2, 536/23.72, 24.3, 24.32, 24.33

[56] References Cited

FOREIGN PATENT DOCUMENTS 318216  5/1989  European Pat. Off. .

OTHER PUBLICATIONS

Holland, J., et al "Rapid Evolution of RNA Genomes", Science (1982), vol. 215, pp. 1577–1585.

*Primary Examiner*—David Guzo
*Attorney, Agent, or Firm*—Beveridge, DeGrandi, Weilacher & Young L.L.P.

[57]  ABSTRACT

The noncoding region, containing at least 324 nucleotides, of the 5' terminus of non-A, non-B hepatitis virus is disclosed. Also disclosed is the nucleotide sequence of the structural gene which is upstream of the noncoding region. Oligonucleotide primers derived from these regions can be used to to detect non-A, non-B hepatitis virus.

21 Claims, 1 Drawing Sheet

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 324 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:1:

```
GGCGACACTC  CACCATAGAT  CACTCCCCTG  TGAGGAACTA  CTGTCTTCAC  GCAGAAAGCG     60
TCTAGCCATG  GCGTTAGTAT  GAGTGTCGTG  CAGCCTCCAG  GACCCCCCT   CCCGGGAGAG    120
CCATAGTGGT  CTGCGGAACC  GGTGAGTACA  CCGGAATTGC  CAGGACGACC  GGGTCCTTTC    180
TTGGATAAAC  CCGCTCAATG  CCTGGAGATT  TGGGCGCGCC  CCCGCAAGAC  TGCTAGCCGA    240
GTAGTGTTGG  GTCGCGAAAG  GCCTTGTGGT  ACTGCCTGAT  AGGGTGCTTG  CGAGTGCCCC    300
GGGAGGTCTC  GTAGACCGTG  CACC                                              324
```

( 2 ) INFORMATION FOR SEQ ID NO:2:

( i ) SEQUENCE CHARACTERISTICS:
        ( A ) LENGTH: 536 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

```
ATGAGCACGA  TTCCCAAACC  TCAAAGAAAA  ACCAAACGTA  ACACCAACCG  TCGCCCACAG     60
GACGTCAAGT  TCCCGGGTGG  CGGTCAGATC  GTTGGTGGAG  TTTACTTGTT  GCCGCGCAGG    120
GGCCCTAGAT  TGGGTGTGCG  CGCGACGAGG  AAGACTTCCG  AGCGGTCGCA  ACCTCGAGGT    180
AGACGTCAGC  CTATCCCCAA  GGTGCGTCGG  CCCGAGGGCA  GGACCTGGGC  TCAGCCCGGG    240
TACCCTTGGC  CCCTCTATGG  CAATGAGGGC  TGCGGGTGGG  CGGGATGGCT  CCTGTCTCCC    300
CGTGGCTCTC  GGCCTAGTTG  GGGCCCCACG  GACCCCGGC   GTAGGTCGCG  CAATTGGGT    360
AAGGTCATCG  ATACCCTCAC  GTGCGGCTTC  GCCGACCTCA  TGGGGTACAT  ACCGCTCGTC    420
GGCGCCCCTC  TTGGAGGCGC  TGCCAGGGCC  CTGGCGCATG  GCGTCCGGGT  TCTGGAAGAC    480
GGCGTGAACT  ATGCAACAGG  GAACCTTCCT  GGTTGCTCTT  TCTCTATCTT  CCTTCT       536
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

```
TAGATTGGGT  GTGCGCGCGA                                                     20
```

( 2 ) INFORMATION FOR SEQ ID NO:4:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: unknown ( i i ) MOLECULE TYPE: DNA (genomic)

( x i ) SEQUENCE DESCRIPTION: SEQ ID NO:4:

TCCCTGTTGC ATAGTTCACG 20

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:5:

ACTCCACCAT AGATCACTCC 20

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:6:

TTCACGCAGA AAGCGTCTAG 20

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:7:

AACACTACTC GGCTAGCAGT 20

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:8:

GTTGATCCAA GAAAGGACCC 20

( 2 ) INFORMATION FOR SEQ ID NO:9:

( i ) SEQUENCE CHARACTERISTICS:
      ( A ) LENGTH: 20 base pairs
      ( B ) TYPE: nucleic acid
      ( C ) STRANDEDNESS: single (D) TOPOLOGY: unknown (ii) MOLECULE TYPE: DNA (genomic)

(xi) SEQUENCE DESCRIPTION: SEQ ID NO:9:

GATGCTTGCG GAAGCAATCA                                                                 20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:10:

GGCGACACTC CACCATAGAT                                                                 20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:11:

CTCATGGGGT ACATTCCGCT                                                                 20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:12:

TCGGTCGTCC CCACCACAAC                                                                 20

(2) INFORMATION FOR SEQ ID NO:13:

(i) SEQUENCE CHARACTERISTICS:
        (A) LENGTH: 1863 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:13:

```
GGCGACACTC  CACCATAGAT  CACTCCCTG   TGAGGAACTA  CTGTCTTCAC  GCAGAAAGCG      60
TCTAGCCATG  GCGTTAGTAT  GAGTGTCGTG  CAGCCTCCAG  GACCCCCCT   CCCGGGAGAG     120
CCATAGTGGT  CTGCGGAACC  GGTGAGTACA  CCGGAATTGC  CAGGACGACC  GGGTCCTTTC     180
TTGGATAAAC  CCGCTCAATG  CCTGGAGATT  TGGGCGCGCC  CCCGCAAGAC  TGCTAGCCGA     240
GTAGTGTTGG  GTCGCGAAAG  GCCTTGTGGT  ACTGCCTGAT  AGGGTGCTTG  CGAGTGCCCC     300
GGGAGGTCTC  GTAGACCGTG  CACCATGAGC  ACGATTCCCA  AACCTCAAAG  AAAAACCAAA     360
CGTAACACCA  ACCGTCGCCC  ACAGGACGTC  AAGTTCCCGG  GTGGCGGTCA  GATCGTTGGT     420
```

| | | | | | |
|---|---|---|---|---|---|
| GGAGTTTACT | TGTTGCCGCG | CAGGGGCCCT | AGATTGGGTG | TGCGCGCGAC | GAGGAAGACT | 480
| TCCGAGCGGT | CGCAACCTCG | AGGTAGACGT | CAGCCTATCC | CCAAGGTGCG | TCGGCCCGAG | 540
| GGCAGGACCT | GGGCTCAGCC | CGGGTACCCT | TGGCCCCTCT | ATGGCAATGA | GGGCTGCGGG | 600
| TGGGCGGGAT | GGCTCCTGTC | TCCCCGTGGC | TCTCGGCCTA | GTTGGGGCCC | CACGGACCCC | 660
| CGGCGTAGGT | CGCGCAATTT | GGGTAAGGTC | ATCGATACCC | TCACGTGCGG | CTTCGCCGAC | 720
| CTCATGGGGT | ACATACCCCT | CGTCGGCGCC | CCTCTTGGAG | GCGCTGCCAG | GGCCCTGGCG | 780
| CATGGCGTCC | GGGTTCTGGA | AGACGGCGTG | AACTATGCAA | CAGGGAACCT | TCCTGGTTGC | 840
| TCTTTCTCTA | TCTTCCTTCT | GGCCCTGCTC | TCTTGCCTGA | CTGTGCCCGC | TTCAGCCTAC | 900
| CAAGTGCGCA | ACTCCACAGG | GCTTTATCAT | GTCACCAATG | ATTGCCCTAA | CTCGAGTATT | 960
| GTGTACGAGG | CGCACGATGC | CATCCTGCAT | ACTCCGGGGT | GTGTCCCTTG | CGTTCGCGAG | 1020
| GGCAACGTCT | CGAGGTGTTG | GGTGGCGATG | ACCCCACGG | TAGCCACCAG | GGACGGCAAA | 1080
| CTCCCCGCGA | CGCAGCTTCG | ACGTCACATC | GATCTGCTTG | TCGGGAGCGC | CACCCTCTGT | 1140
| TCGGCCCTCT | ACGTGGGGGA | TCTGTGCGGG | TCCGTCTTCC | TTATTGGTCA | ACTGTTTACC | 1200
| TTCTCTCCCA | GGCGCCACTG | GACAACGCAA | GGCTGCAATT | GTTCTATCTA | CCCCGGCCAT | 1260
| ATAACGGGTC | ATCGCATGGC | ATGGGATATG | ATGATGAACT | GGTCCCTAC | GGCGGCGTTG | 1320
| GTAATGGCTC | AGCTGCTCCG | GATCCACAA | GCCATCTTGG | ATATGATCGC | TGGTGCTCAC | 1380
| TGGGGAGTCC | TGGCGGGCAT | AGCGTATTTC | TCCATGGTGG | GGAACTGGGC | GAAGGTCCTG | 1440
| GTAGTGCTGT | TGCTGTTTGC | CGGCGTCGAC | GCGGAAACCA | TCGTCTCCGG | GGGACAAGCC | 1500
| GCCCGCGCCA | TGTCTGGACT | TGTTAGTCTC | TTCACACCAG | GCGCTAAGCA | GAACATCCAG | 1560
| CTGATCAACA | CCAACGGCAG | TTGGCACATC | AATAGCACGG | CCTTGAACTG | CAATGAAAGC | 1620
| CTTAACACCG | GCTGGTTAGC | AGGGCTTATC | TATCAACACA | AATTCAACTC | TTCGGGCTGT | 1680
| CCCGAGAGGT | TGGCCAGCTG | CCGACGCCTT | ACCGATTTTG | ACCAGGGCTG | GGGCCCTATC | 1740
| AGTCATGCCA | ACGGAAGCGG | CCCCGACCAA | CGCCCTATT | GTTGGCACTA | CCCCCCAAAA | 1800
| CCTTGCGGTA | TCGTGCCCGC | AAAGAGCGTA | TGTGGCCCGG | TATATTGCTT | CACTCCCAGC | 1860
| CCC | | | | | | 1863

(2) INFORMATION FOR SEQ ID NO:14:

(i) SEQUENCE CHARACTERISTICS:
        (A) LENGTH: 1863 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:14:

| | | | | | |
|---|---|---|---|---|---|
| GGCGACACTC | CACCATAGAT | CACTCCCCTG | TGAGGAACTA | CTGTCTTCAC | GCAGAAAGCG | 60
| TCTAGCCATG | GCGTTAGTAT | GAGTGTCGTG | CAGCCTCCAG | GACCCCCCT | CCCGGGAGAG | 120
| CCATAGTGGT | CTGCGGAACC | GGTGAGTACA | CCGGAATTGC | CAGGACGACC | GGGTCCTTTC | 180
| TTGGATCAAC | CCGCTCAATG | CCTGGAGATT | TGGGCGTGCC | CCCGCGAGAC | TGCTAGCCGA | 240
| GTAGTGTTGG | GTCGCGAAAG | GCCTTGTGGT | ACTGCCTGAT | AGGGTGCTTG | CGAGTGCCCC | 300
| GGGAGGTCTC | GTAGACCGTG | CACCATGAGC | ACGAATCCTA | AACCTCAAAG | AAAAACCAAA | 360
| CGTAACACCA | ACCGCCGCCC | ACAGGACGTC | AAGTTCCCGG | GCGGTGGTCA | GATCGTTGGT | 420
| GGAGTTTACC | TGTTGCCGCG | CAGGGGCCCC | AGGTTGGGTG | TGCGCGCGAC | TAGGAAGACT | 480
| TCCGAGCGGT | CGCAACCTCG | TGGATGGCGA | CAACCTATCC | CCAAGGCTCG | CCGACCCGAG | 540

-continued

| | | | | | | |
|---|---|---|---|---|---|---|
|GGCAGGGCCT|GGGCTCAGCC|CGGGTACCCT|TGGCCCCTCT|ATGGCAATGA|GGGCTTGGGG|600|
|TGGGCAGGAT|GGCTCCTGTC|ACCCCGCGGC|TCCCGGCCTA|GTTGGGGCCC|CACGGACCCC|660|
|CGGCGTAGGT|CGCGTAACTT|GGGTAAGGTC|ATCGATACCC|TTACATGCGG|CTTCGCCGAT|720|
|CTCATGGGGT|ATATTCCCCT|CGTCGGCGCC|CCCCTAGGGG|GCGCTGCCAG|GGCCTTGGCA|780|
|CACGGTGTCC|GGGTTCTGGA|GGACGGCGTG|AACTATGCAA|CAGGGAACTT|GCCCGGTTGC|840|
|TCTTTCTCTA|TCTTCCTCTT|GGCTTTGCTG|TCCTGTTTGA|CCATCCCAGC|TTCCGCTTAT|900|
|GAAGTGCGCA|ACGTGTCCGG|GATATACCAT|GTCACGAACG|ACTGCTCCAA|CTCAAGCATT|960|
|GTGTATGAGG|CAGCGGACAT|GATCATGCAT|ACTCCCGGGT|GCGTGCCCTG|CGTTCGGGAG|1020|
|GACAACAGCT|CCCGTTGCTG|GGTAGCGCTC|ACTCCCACGC|TCGCGGCCAG|GAATGCCAGG|1080|
|GTCCCCACTA|CGACAATACG|ACGCCACGTC|GACTTGCTCG|TTGGGCGGC|TGCTTTCTGC|1140|
|TCCGCTATGT|ACGTGGGGGA|TCTCTGCGGA|TCTGTTTTCC|TCGTCTCCCA|GCTGTTCACC|1200|
|TTCTCGCCTC|GCCGGCATGA|GACAGTGCAG|GACTGCAACT|GCTCAATCTA|TCCCGGCCAT|1260|
|TTATCAGGTC|ACCGCATGGC|TTGGGATATG|ATGATGAACT|GGTCACCTAC|AACAGCCCTA|1320|
|GTGGTGTCGC|AGTTGCTCCG|GATCCACAA|GCTGTCGTGG|ACATGGTGGC|GGGGGCCCAC|1380|
|TGGGGAGTCC|TGGCGGGCCT|TGCCTACTAT|TCCATGGTAG|GGAACTGGGC|TAAGGTCCTG|1440|
|ATTGTGGCGC|TACTCTTCGC|CGGCGTTGAC|GGGGAGACCT|ACACGTCGGG|GGGAGGCGCC|1500|
|AGCCACACCA|CCTCCACGCT|CGCGTCCCTC|TTCTCACCTG|GGCGTCTCA|GAGAATCCAG|1560|
|CTTGTGAATA|CCAACGGCAG|CTGGCACATC|AACAGGACTG|CCCTAAACTG|CAATGACTCC|1620|
|CTCCACACTG|GGTTCCTTGC|CGCGCTGTTC|TACACACA|GGTTCAACTC|GTCCGGGTGC|1680|
|CCGGAGCGCA|TGGCCAGCTG|CCGCCCCATT|GACTGGTTCG|CCCAGGGATG|GGGCCCCATC|1740|
|ACCTATACTG|AGCCTGACAG|CCCGGATCAG|AGGCCTTATT|GCTGGCATTA|CGCGCCTCGA|1800|
|CCGTGTGGTA|TCGTACCCGC|GTCGCAGGTG|TGTGGTCCAG|TGTATTGCTT|CACCCCAAGC|1860|
|CCT| | | | | |1863|

(2) INFORMATION FOR SEQ ID NO:15:

(i) SEQUENCE CHARACTERISTICS:
        (A) LENGTH: 324 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:15:

| | | | | | | |
|---|---|---|---|---|---|---|
|GGCGACACTC|CACCATAGAT|CACTCCCCTG|TGAGGAACTA|CTGTCTTCAC|GCAGAAAGCG|60|
|TCTAGCCATG|GCGTTAGTAT|GAGTGTCGTG|CAGCCTCCAG|GACCCCCCT|CCCGGGAGAG|120|
|CCATAGTGGT|CTGCGGAACC|GGTGAGTACA|CCGGAATTGC|CAGGACGACC|GGGTCCTTTC|180|
|TTGGATCAAC|CCGCTCAATG|CCTGGAGATT|TGGGCGTGCC|CCCGCGAGAC|TGCTAGCCGA|240|
|GTAGTGTTGG|GTCGCGAAAG|GCCTTGTGGT|ACTGCCTGAT|AGGGTGCTTG|CGAGTGCCCC|300|
|GGGAGGTCTC|GTAGACCGTG|CACC| | | |324|

(2) INFORMATION FOR SEQ ID NO:16:

(i) SEQUENCE CHARACTERISTICS:
        (A) LENGTH: 1539 base pairs
        (B) TYPE: nucleic acid
        (C) STRANDEDNESS: single
        (D) TOPOLOGY: unknown ( i i ) MOLECULE TYPE: DNA (genomic)

( x i ) SEQUENCE DESCRIPTION: SEQ ID NO:16:

| | | | | | |
|---|---|---|---|---|---|
| ATGAGCACGA | TTCCCAAACC | TCAAAGAAAA | ACCAAACGTA | ACACCAACCG | TCGCCCACAG | 60
| GACGTCAAGT | TCCCGGGTGG | CGGTCAGATC | GTTGGTGGAG | TTTACTTGTT | GCCGCGCAGG | 120
| GGCCCTAGAT | TGGGTGTGCG | CGCGACGAGG | AAGACTTCCG | AGCGGTCGCA | ACCTCGAGGT | 180
| AGACGTCAGC | CTATCCCCAA | GGTGCGTCGG | CCCGAGGGCA | GGACCTGGGC | TCAGCCCGGG | 240
| TACCCTTGGC | CCCTCTATGG | CAATGAGGGC | TGCGGGTGGG | CGGGATGGCT | CCTGTCTCCC | 300
| CGTGGCTCTC | GGCCTAGTTG | GGGCCCCACG | GACCCCGGC | GTAGGTCGCG | CAATTTGGGT | 360
| AAGGTCATCG | ATACCCTCAC | GTGCGGCTTC | GCCGACCTCA | TGGGGTACAT | ACCCCTCGTC | 420
| GGCGCCCCTC | TTGGAGGCGC | TGCCAGGGCC | CTGGCGCATG | GCGTCCGGGT | TCTGGAAGAC | 480
| GGCGTGAACT | ATGCAACAGG | GAACCTTCCT | GGTTGCTCTT | TCTCTATCTT | CCTTCTGGCC | 540
| CTGCTCTCTT | GCCTGACTGT | GCCCGCTTCA | GCCTACCAAG | TGCGCAACTC | CACAGGGCTT | 600
| TATCATGTCA | CCAATGATTG | CCCTAACTCG | AGTATTGTGT | ACGAGGCGCA | CGATGCCATC | 660
| CTGCATACTC | CGGGGTGTGT | CCCTTGCGTT | CGCGAGGGCA | ACGTCTCGAG | GTGTTGGGTG | 720
| GCGATGACCC | CCACGGTAGC | CACCAGGGAC | GGCAAACTCC | CCGCGACGCA | GCTTCGACGT | 780
| CACATCGATC | TGCTTGTCGG | GAGCGCCACC | CTCTGTTCGG | CCCTCTACGT | GGGGGATCTG | 840
| TGCGGGTCCG | TCTTCCTTAT | TGGTCAACTG | TTTACCTTCT | CTCCCAGGCG | CCACTGGACA | 900
| ACGCAAGGCT | GCAATTGTTC | TATCTACCCC | GGCCATATAA | CGGGTCATCG | CATGGCATGG | 960
| GATATGATGA | TGAACTGGTC | CCCTACGGCG | GCGTTGGTAA | TGGCTCAGCT | GCTCCGGATC | 1020
| CCACAAGCCA | TCTTGGATAT | GATCGCTGGT | GCTCACTGGG | GAGTCCTGGC | GGGCATAGCG | 1080
| TATTTCTCCA | TGGTGGGGAA | CTGGGCGAAG | GTCCTGGTAG | TGCTGTTGCT | GTTTGCCGGC | 1140
| GTCGACGCGG | AAACCATCGT | CTCCGGGGA | CAAGCCGCCC | GCGCCATGTC | TGGACTTGTT | 1200
| AGTCTCTTCA | CACCAGGCGC | TAAGCAGAAC | ATCCAGCTGA | TCAACACCAA | CGGCAGTTGG | 1260
| CACATCAATA | GCACGGCCTT | GAACTGCAAT | GAAAGCCTTA | ACACCGGCTG | GTTAGCAGGG | 1320
| CTTATCTATC | AACACAAATT | CAACTCTTCG | GGCTGTCCCG | AGAGGTTGGC | CAGCTGCCGA | 1380
| CGCCTTACCG | ATTTTGACCA | GGGCTGGGGC | CCTATCAGTC | ATGCCAACGG | AAGCGGCCCC | 1440
| GACCAACGCC | CCTATTGTTG | GCACTACCCC | CCAAAACCTT | GCGGTATCGT | GCCCGCAAAG | 1500
| AGCGTATGTG | GCCCGGTATA | TTGCTTCACT | CCCAGCCCC | | | 1539

( 2 ) INFORMATION FOR SEQ ID NO:17:

( i ) SEQUENCE CHARACTERISTICS:
        ( A ) LENGTH: 1539 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:17:

| | | | | | |
|---|---|---|---|---|---|
| ATGAGCACGA | ATCCTAAACC | TCAAAGAAAA | ACCAAACGTA | ACACCAACCG | CCGCCCACAG | 60
| GACGTCAAGT | TCCCGGGCGG | TGGTCAGATC | GTTGGTGGAG | TTTACCTGTT | GCCGCGCAGG | 120
| GGCCCCAGGT | TGGGTGTGCG | CGCGACTAGG | AAGACTTCCG | AGCGGTCGCA | ACCTCGTGGA | 180
| TGGCGACAAC | CTATCCCCAA | GGCTCGCCGA | CCCGAGGGCA | GGGCCTGGGC | TCAGCCCGGG | 240
| TACCCTTGGC | CCCTCTATGG | CAATGAGGGC | TTGGGGTGGG | CAGGATGGCT | CCTGTCACCC | 300

| | | | | | | |
|---|---|---|---|---|---|---|
| CGCGGCTCCC | GGCCTAGTTG | GGGCCCCACG | GACCCCGGC | GTAGGTCGCG | TAACTTGGGT | 360 |
| AAGGTCATCG | ATACCCTTAC | ATGCGGCTTC | GCCGATCTCA | TGGGGTATAT | TCCCCTCGTC | 420 |
| GGCGCCCCCC | TAGGGGCGC | TGCCAGGGCC | TTGGCACACG | GTGTCCGGGT | TCTGGAGGAC | 480 |
| GGCGTGAACT | ATGCAACAGG | GAACTTGCCC | GGTTGCTCTT | TCTCTATCTT | CCTCTTGGCT | 540 |
| TTGCTGTCCT | GTTTGACCAT | CCCAGCTTCC | GCTTATGAAG | TGCGCAACGT | GTCCGGGATA | 600 |
| TACCATGTCA | CGAACGACTG | CTCCAACTCA | AGCATTGTGT | ATGAGGCAGC | GGACATGATC | 660 |
| ATGCATACTC | CCGGGTGCGT | GCCCTGCGTT | CGGGAGGACA | ACAGCTCCG | TTGCTGGGTA | 720 |
| GCGCTCACTC | CCACGCTCGC | GGCCAGGAAT | GCCAGGGTCC | CCACTACGAC | AATACGACGC | 780 |
| CACGTCGACT | TGCTCGTTGG | GGCGGCTGCT | TTCTGCTCCG | CTATGTACGT | GGGGGATCTC | 840 |
| TGCGGATCTG | TTTTCCTCGT | CTCCCAGCTG | TTCACCTTCT | CGCCTCGCCG | GCATGAGACA | 900 |
| GTGCAGGACT | GCAACTGCTC | AATCTATCCC | GGCCATTTAT | CAGGTCACCG | CATGGCTTGG | 960 |
| GATATGATGA | TGAACTGGTC | ACCTACAACA | GCCCTAGTGG | TGTCGCAGTT | GCTCCGGATC | 1020 |
| CCACAAGCTG | TCGTGGACAT | GGTGGCGGGG | GCCCACTGGG | GAGTCCTGGC | GGGCCTTGCC | 1080 |
| TACTATTCCA | TGGTAGGGAA | CTGGGCTAAG | GTCCTGATTG | TGGCGCTACT | CTTCGCCGGC | 1140 |
| GTTGACGGGG | AGACCTACAC | GTCGGGGGGA | GGCGCCAGCC | ACACCACCTC | CACGCTCGCG | 1200 |
| TCCCTCTTCT | CACCTGGGGC | GTCTCAGAGA | ATCCAGCTTG | TGAATACCAA | CGGCAGCTGG | 1260 |
| CACATCAACA | GGACTGCCCT | AAACTGCAAT | GACTCCCTCC | ACACTGGGTT | CCTTGCCGCG | 1320 |
| CTGTTCTACA | CACACAGGTT | CAACTCGTCC | GGGTGCCCGG | AGCGCATGGC | CAGCTGCCGC | 1380 |
| CCCATTGACT | GGTTCGCCCA | GGGATGGGGC | CCCATCACCT | ATACTGAGCC | TGACAGCCCG | 1440 |
| GATCAGAGGC | CTTATTGCTG | GCATTACGCG | CCTCGACCGT | GTGGTATCGT | ACCCGCGTCG | 1500 |
| CAGGTGTGTG | GTCCAGTGTA | TTGCTTCACC | CCAAGCCCT | | | 1539 |

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:18:

AAACCTTGCG GTATTGTGCC                                                                                     20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:19:

AGTGTGTGTG GTCCGGTATA                                                                                     20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:20:

CGGTGGCCTG GTATTGTTAA          20

( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:21:

GAGTTCATCC GGTACAACC          19

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:22:

AGATGGCTTT GTACGACGTG          20

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:23:

TCCAATACTC ACCAGGACAG          20

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:24:

CACAGCTAGT TGTCAGTACG          20

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:25:

TTGATGTAGC AAGTGAGGGT 20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:26:

CTGGTGACAG CAGCTGTAAA 20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:27:

TGAAGAGGAG GGTTTGGCTA 20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:28:

TATTGCCTGT CAACAGGCTG 20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:29:

CGAGAGTTCG ATGAGATGGA 20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:30:

AAGACTTCCG AGCGGTCGCA 20

(2) INFORMATION FOR SEQ ID NO:31:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:31:

TTGCCATAGA GGGGCCAAGG                                                                                           20

( 2 ) INFORMATION FOR SEQ ID NO:32:

( i ) SEQUENCE CHARACTERISTICS:
        ( A ) LENGTH: 540 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:32:

ATGAGCACGA TTCCCAAACC TCAAAGAAAA ACCAAACGTA ACACCAACCG TCGCCCACAG    60

GACGTCAAGT TCCCGGGTGG CGGTCAGATC GTTGGTGGAG TTTACTTGTT GCCGCGCAGG   120

GGCCCTAGAT TGGGTGTGCG CGCGACGAGG AAGACTTCCG AGCGGTCGCA ACCTCGAGGT   180

AGACGTCAGC CTATCCCCAA GGTGCGTCGG CCCGAGGGCA GGACCTGGGC TCAGCCCGGG   240

TACCCTTGGC CCCTCTATGG CAATGAGGGC TGCGGGTGGG CGGGATGGCT CCTGTCTCCC   300

CGTGGCTCTC GGCCTAGTTG GGGCCCCACG GACCCCGGC GTAGGTCGCG CAATTTGGGT    360

AAGGTCATCG ATACCCTCAC GTGCGGCTTC GCCGACCTCA TGGGTACAT ACCCCTCGTC    420

GGCGCCCCTC TTGGAGGCGC TGCCAGGGCC CTGGCGCATG GCGTCCGGGT TCTGGAAGAC   480

GGCGTGAACT ATGCAACAGG GAACCTTCCT GGTTGCTCTT TCTCTATCTT CCTTCTGGCC   540

( 2 ) INFORMATION FOR SEQ ID NO:33:

( i ) SEQUENCE CHARACTERISTICS:
        ( A ) LENGTH: 999 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:33:

CTGCTCTCTT GCCTGACTGT GCCCGCTTCA GCCTACCAAG TGCGCAACTC CACAGGGCTT    60

TATCATGTCA CCAATGATTG CCCTAACTCG AGTATTGTGT ACGAGGCGCA CGATGCCATC   120

CTGCATACTC CGGGGTGTGT CCCTTGCGTT CGCGAGGGCA ACGTCTCGAG GTGTTGGGTG   180

GCGATGACCC CCACGGTAGC CACCAGGGAC GGCAAACTCC CCGCGACGCA GCTTCGACGT   240

CACATCGATC TGCTTGTCGG GAGCGCCACC CTCTGTTCGG CCCTCTACGT GGGGGATCTG   300

TGCGGGTCCG TCTTCCTTAT TGGTCAACTG TTTACCTTCT CTCCAGGCG CCACTGGACA    360

ACGCAAGGCT GCAATTGTCC TATCTACCCC GGCCATATAA CGGGTCATCG CATGGCATGG   420

GATATGATGA TGAACTGGTC CCCTACGGCG GCGTTGGTAA TGGCTCAGCT GCTCCGGATC   480

CCACAAGCCA TCTTGGATAT GATCGCTGGT GCTCACTGGG GAGTCCTGGC GGGCATAGCG   540

TATTTCTCCA TGGTGGGGAA CTGGGCGAAG GTCCTGGTAG TGCTGTTGCT GTTTGCCGGC   600

GTCGACGCGG AAACCATCGT CTCCGGGGA CAAGCCGCCC GCGCCATGTC TGGACTTGTT    660

AGTCTCTTCA CACCAGGCGC TAAGCAGAAC ATCCAGCTGA TCAACACCAA CGGCAGTTGG   720

-continued

| | | | | | | |
|---|---|---|---|---|---|---|
| CACATCAATA | GCACGGCCTT | GAACTGCAAT | GAAAGCCTTA | ACACCGGCTG | GTTAGCAGGG | 780 |
| CTTATCTATC | AACACAAATT | CAACTCTTCG | GGCTGTCCCG | AGAGGTTGGC | CAGCTGCCGA | 840 |
| CGCCTTACCG | ATTTTGACCA | GGGCTGGGGC | CCTATCAGTC | ATGCCAACGG | AAGCGGCCCC | 900 |
| GACCAACGCC | CCTATTGTTG | GCACTACCCC | CCAAAACCTT | GCGGTATCGT | GCCCGCAAAG | 960 |
| AGCGTATGTG | GCCCGGTATA | TTGCTTCACT | CCCAGCCCC | | | 999 |

OLIGONUCLEOTIDE PRIMERS, AND THEIR APPLICATION FOR HIGH-FIDELITY DETECTION OF NON-A, NON-B HEPATITIS VIRUS

This is a divisional of co-pending application Ser. No. 07/712,875 filed on Jun. 11, 1991.

INTRODUCTION TO THE INVENTION

The present invention concerns high-fidelity detection of non-A, non-B hepatitis virus (hereinafter called NANB hepatitis virus) and oligonucleotide primers used in a detection system for detecting NANB hepatitis virus.

Viral hepatitis of which DNA and RNA have been elucidated include hepatitis A, hepatitis B, hepatitis D and hepatitis E. However, in spite of great efforts by scientists the world over, the causative virus of NANB hepatitis (which is mainly caused by blood bourne infection) falls in none of the above groups and has not been isolated.

In 1988, Chiron Corp. reported that it had succeeded in cloning the RNA virus genome of the causative agent of NANB hepatitis (which it termed hepatitis C virus (hereinafter called HCV)) and disclosed part of the nucleotide sequence of HCV. HCV antibody detection systems based on that sequence are now being introduced for screening of blood for transfusion and for diagnosis of patients.

However, the nucleotide sequence disclosed by Chiron Corp. was only part of the NANB hepatitis viral genome. Moreover, it was part of a sequence of relatively little importance. HCV antibody detection systems developed on the basis of that sequence, therefore, fail to provide both sufficient sensitivity and specificity for NANB hepatitis virus and for therapy and prognosis of acute and chronic NANB hepatitis, although such systems have proven their partial association with NANB hepatitis.

More than 95% of posttransfusion hepatitis cases in Japan are NANB hepatitis. There are 280,000 annual estimated cases of this disease. The course of NANB hepatitis is troublesome, with most patients becoming carriers who develop chronic hepatitis. In addition, those patients with chronic hepatitis develop liver cirrhosis and then hepatocellular carcinoma at a fairly high rate over 10 to 20 years. Therefore it is imperative to isolate the virus itself and to develop effective diagnostic reagents enabling earlier diagnosis.

As described earlier, there are significant numbers of patients with acute or chronic NANB hepatitis which can not be diagnosed by the detection systems using Chiron's HCV antibody. For accurate diagnosis of these cases of hepatitis, detection systems for the virus based on elucidation of the viral agent at its gene level is required.

SUMMARY OF THE INVENTION

An object of the present invention is to provide a highly sensitive detection system for NANB hepatitis virus at its gene level and oligonucleotide primers used for such system.

DETAILED DESCRIPTION OF THE INVENTION

Figure 1:
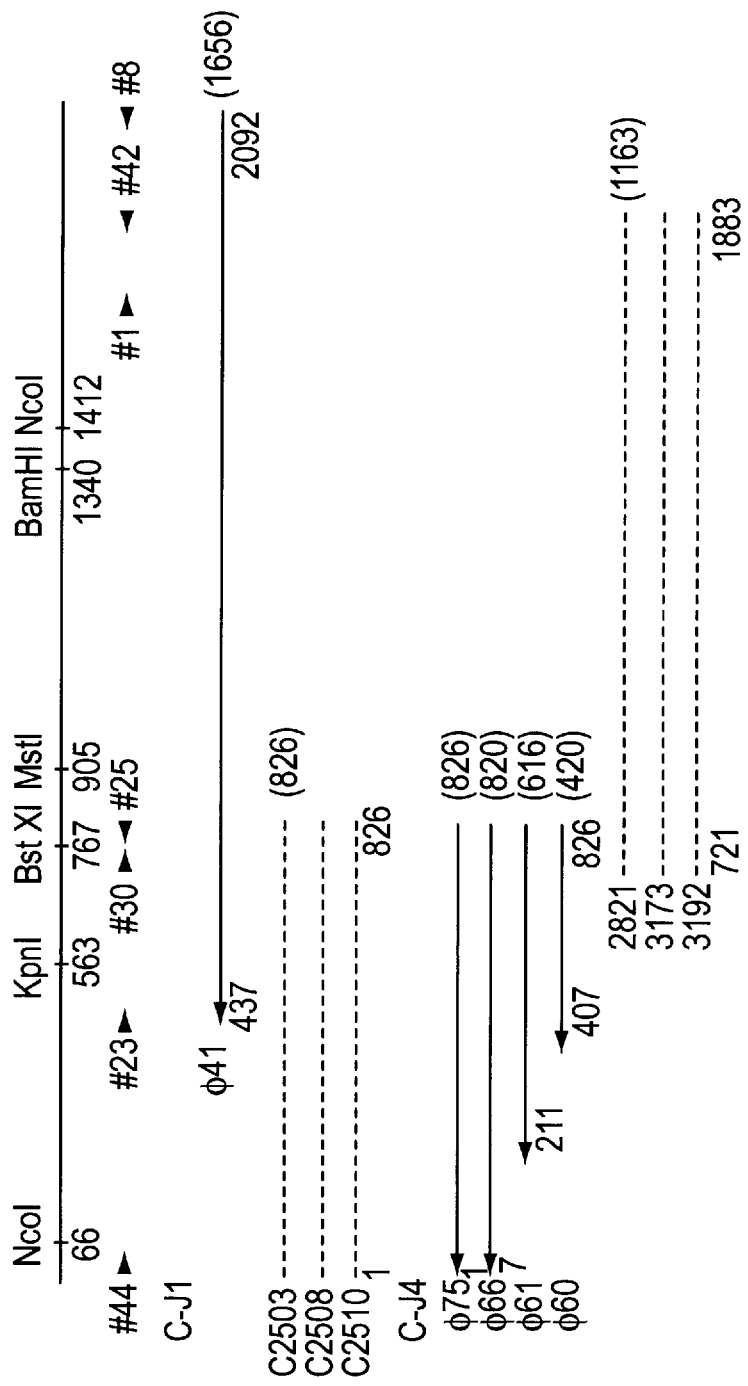
FIG. 1 shows determination method of nucleotide sequences of NANB hepatitis viral RNA.

For the purpose of elucidation of the NANB hepatitis viral gene, the inventors isolated NANB hepatitis viral RNA from human and chimpanzee carrier sera and determined the nucleotide sequence of the 5' terminus by cloning its cDNA. As a result, the inventors identified that for two different strains the RNA genome had a 5' noncoding region having a sequence of at least 324 nucleotides. This sequence had not been disclosed by Chiron and is totally novel. It was also determined that the nucleotide sequence in this region was highly conserved among different strains. For example, the RNA of strains HC-J1 and HC-J4 (used for the determination of the nucleotide sequence) differed from each other by only three nucleotides.

On the other hand, large differences (or mutations) in nucleotides were identified in other regions of NANB hepatitis viral RNA. When this fact is taken into consideration, it is amazing that the nucleotide sequence is conserved so well in the 5' noncoding region. It was further determined that there were few differences in the nucleotide sequence in the upstream part of the structural gene following the noncoding region. Based on these findings, the inventors discovered that use of oligonucleotide primers derived from these regions would detect, with high sensitivity, NANB hepatitis RNA irrespective of the strain.

The present invention, therefore, concerns a NANB hepatitis virus detection system using oligonucleotide primers having nucleotide sequences corresponding to part of the 5' noncoding region of the viral RNA and/or part of the 5' side of the region coding for the structural protein of the virus. The primers can contain from about 15 to about 25 nucleotides, preferably 20.

Abbreviations used in this invention are as follows: for RNA, A, G, C and U stand for adenine, guanine, cytosine and uracil respectively; for DNA, A, G and C indicate the same bases as in RNA and T stands for thymine; for polypeptides, A, R, N, D, C, E, Q, G, H, I, L, K, M, F, P, S, T, W, Y and V are respectively the amino acids of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

The inventors have identified that the 5' noncoding region has the following nucleotide sequence (HC-J1 strain) SEQ ID NO:1:

```
GGCGACACTC CACCATAGAT
CACTCCCCTG TGAGGAACTA
CTGTCTTCAC GCAGAAAGCG
TCTAGCCATG GCGTTAGTAT
GAGTGTCGTG CAGCCTCCAG  100
GACCCCCCCT CCCGGGAGAG
CCATAGTGGT CTGCGGAACC
GGTGAGTACA CCGGAATTGC
CAGGACGACC GGGTCCTTTC
TTGGATAAAC CCGCTCAATG  200
CCTGGAGATT TGGGCGCGCC
CCCGCAAGAC TGCTAGCCGA
GTAGTGTTGG GTCGCCAAAG
GCCTTGTGGT ACTGCCTGAT
```

-continued
```
AGGGTGCTTG CGAGTGCCCC    300

GGGAGGTCTC GTAGACCGTG

CACC
```

The inventors have further determined that the remaining sequence of the 5' noncoding region of the HC-J4 strain is identical to that of HC-J1 (except for the 187th nucleotide A which is replaced by C, the 217th nucleotide C which is replaced by T, and the 226th nucleotide A which is replaced by G). The inventors subsequently developed the highly sensitive detection system for NANB hepatitis virus using oligonucleotide primers corresponding to part of the 5' noncoding region of NANB hepatitis virus. Therefore, any oligonucleotide primer belonging to this defined region of HCV genome may be included in this invention, though replacement of one or more nucleotides is also included.

The inventors have also identified that the upstream region coding for the structural protein of the virus following the aforementioned 5' noncoding region was well conserved among the strains. There were only a few differences between the strains. Nucleotide sequences corresponding to part of that region, used as primers, can detect NANB hepatitis virus with high sensitivity.

The upstream region of the structural gene of the NANB hepatitis virus has the following nucleotide sequence (for the HC-J1 strain) (SEQ ID NO:2:

```
ATGAGC ACGATTCCCA

AACCTCAAAG AAAAACCAAA

CGTAACACCA ACCGTCGCCC

ACAGGACGTC AAGTTCCCGG     400

GTGGCGGTCA GATCGTTGGT

GGAGTTTACT TGTTGCCGCG

CAGGGGCCCT AGATTGGGTG

TGCGCGCGAC GAGGAAGACT

TCCGAGCGGT CCCAACCTCG     500

AGGTAGACGT CAGCCTATCC

CCAAGGTGCG TCGGCCCGAG

GGCAGGACCT GGGCATCGCC

CGGGTACCCT TGGCCCCTCT

ATGGCAATGA GGGCTGCGGG     600

TGGGCGGGAT GGCTCCTGTC

TCCCCGTGGC TCTCGGCCTA

GTTGGGCCC CACGGACCCC

CGGCGTAGGT CGCGCAATTT

GGGTAAGGTC ATCGATACCC     700

TCACGTGCGG CTTCGCCGAC

CTCATGGGGT ACATACCGCT

CGTCGGCGCC CCTCTTGGAG

GCGCTGCCAG GGCCCTGGCG
```

-continued
```
CATGGCGTCC GGGTTCTGGA    800

AGACGGCGTG AACTATGCAA

CAGGGAACCT TCCTGGTTGC

TCTTTCTCTA TCTTCCTTCT
```

Except for the following differences, the upstream region of strain HC-J4 has the same nucleotide sequence as HC-J1 (numbers in parenthesis show respective differences in the sequence from the 5' noncoding region):

| | | | |
|---|---|---|---|
| A (335), | T (339), | C (375), | C (402), |
| T (405), | C (430), | C (450), | G (453), |
| T (471), | T (501), | A (504), | T (505), |
| G (507), | A (510), | A (513), | C (527), |
| T (528), | C (531), | A (534), | G (547), |
| T (596), | G (597), | A (606), | A (621), |
| C (627), | C (633), | T (675), | C (678), |
| T (701), | A (705), | T (720), | T (732), |
| T (734), | C (753), | A (756), | G (759), |
| T (775), | A (780), | C (783), | T (786), |
| G (801), | T (829), | G (831), | C (834), |
| C (858), | T (859). | | |

As far as oligonucleotides corresponding to part of the upstream region of the structural gene of the virus is concerned, also included are nucleotide sequences with a small number of nucleotides different from strains HC-J1 and HC-J4.

This invention includes detection of NANB hepatitis virus by amplification of cDNA of the viral RNA by Polymerase Chain Reaction (hereinafter called PCR) using oligonucleotide primers disclosed herein. PCR is a method well known in this art.

Under optimum conditions, using the product of the first amplification of cDNA by PCR as a template, a second amplification by PCR is carried out. In the second PCR amplification, a pair of primers that can be annealed inside the first pair of primers is used.

The present invention includes oligonucleotide primers used in the above described detection system. This invention also includes creation of oligonucleotide primers having nucleotide sequences corresponding to part of the 5' noncoding region of NANB hepatitis viral RNA genome (having at least 324 nucleotides), and creation of oligonucleotide primers having nucleotide sequences specific to part of the 5' region coding for the structural protein of the virus.

The following primers are particularly preferable (numbers in parenthesis show positions in sequence from the 5' noncoding region):

23: TAGATTGGGTGTGCGCGCGA (450–469 of strain HC-J1) (SEQ ID NO: 3)
25: TCCCTGTTGCATAGTTCACG (807–826)(SEQ ID NO: 4)

32: ACTCCACCATAGATCACTCC ( 7– 26)(SEQ ID NO:5)

33: TTCACGCAGAAAGCGTCTAG ( 46– 65)(SEQ ID NO:6)

36: AACACTACTCGGCTAGCAGT (229–248)(SEQ ID NO: 7) and

48: GTTGATCCAAGAAAGGACCC (171–190)(SEQ ID NO: 8).

When the above primers are in use in PCR, combined use (e.g., of #23 and #25, #32 and #36, or #33 and #48) can enhance the effect of PCR.

This invention also covers NANB hepatitis virus detection systems (e.g., PCR) using the above oligonucleotide primers.

Examples of application of this invention are shown below. However, this invention shall in no way be limited to those examples.

EXAMPLES

Example 1

Determination of the nucleotide sequence of the 5' terminus of NANB hepatitis virus:

(1) Isolation of RNA

RNA was isolated by the method described below from a plasma sample (HC-J1) of a Japanese blood donor who tested positive for HCV antibody and a sample (HC-J4) from a chimpanzee challenged with NANB hepatitis for infectivity but which tested negative for HCV antibody by Ortho HCV Ab ELISA Test (Ortho Diagnostic Systems, Tokyo, Japan).

1.8 ml of each of the plasma samples was added with 1 ml of Tris chloride buffer (10 mM, pH 8.0) and centrifuged at 68×10³ rpm for 1 hour. The precipitate was suspended in Tris chloride buffer (50 mM, pH 8.0) containing 200 mM NaCl, 10 mM EDTA, 2% (w/v) sodium dodecyl sulfate (SDS) and proteinase K (1 mg/ml), incubated at 60° C. for 1 hour, then extracted by phenol/chloroform and precipitated by ethanol to obtain RNAs.

(2) cDNA synthesis

RNA isolated from HC-J1 plasma was incubated at 70° C. for 1 minute and used as a template. 10 units of reverse transcriptase (cDNA Synthesis Plus, Amersham Japan) and 20 pmol of oligonucleotide primer (20 mer) were added and incubated at 42° C. for 1.5 hours to obtain cDNA. Primer #8 (5'-G A T G C T T G C G G A A G C A A T C A-3') SEQ ID NO:9 was prepared by referring to the base sequence shown in FIG. 47-1 (sequence position 401 to 420) of the European Patent Application No. 88310922.5 (the entire application (now European Patent No. 0,318,216) is incorporated by reference).

(3) cDNA was amplified by the following Polymerase Chain Reaction (PCR).

cDNA was amplified for 35 cycles according to Saiki's method (*Science* 239, 487–491 (1988)), incorporated by reference in its entirety, using Gene Amp DNA Amplifier Reagent (Perkin-Elmer Cetus) on a DNA Thermal Cycler (Perkin-Elmer Cetus).

(4) Determination of nucleotide sequence by assembling cDNA clones.

As shown in FIG. 1, the nucleotide sequence of the 5' termini of the genomes of strains HC-J1 and HC-J4 were determined by combined analysis of clones obtained from the cDNA library constructed in bacteriophage lambda gt10 and clones obtained by amplification of HCV specific cDNA by PCR. FIG. 1 shows the 5' terminal sequence of NANB hepatitis virus genome together with cleavage sites of restriction endonucleases and sequences of primers used. In FIG. 1, solid lines are nucleotide sequences determined by clones from bacteriophage lambda gt10 library while dotted lines show sequences determined by clones obtained by PCR.

The 1673 nucleotide sequence of HC-J1, spanning nt437-2092, was determined by the clone φ41 obtained by inserting the cDNA synthesized with the primer #8 into bacteriophage lambda gt10 (Amersham).

Primer #25 (5'-T C C C T G T T G C A T A G T T C A C G-3') (SEQ ID NO:4) of nt 807–826 was synthesized based on that φ41 sequence, and 4 clones (φ60, φ61, φ66 and φ75) were obtained to cover the upstream sequence nt1–826.

The upstream sequence of strain HC-J1 was determined by clones obtained by PCR using primers #44 (5'-G G C G A C A C T C C A C C A T A G A T-3') (SEQ ID NO:10) and #25 (5'-T C C C T G T T G C A T A G T T C A C G-3') (SEQ ID NO:4).

The downstream sequence of 1163 nucleotides, from nt721 up to 1883, of strain HC-J4 was determined by 3 clones (C2821, C3173 and C3192) by PCR using primers #30 (5'-C T C A T G G G G T A C A T T C C G C T-3') (SEQ ID NO:11) and #42 (5'-T C G G T C G T C C C C A C C A C A A C-3') (SEQ ID NO:12).

From the analysis described above, nucleotide sequences of the 5' termini of the genomes of strains HC-J1 and HC-J4 were determined as shown below.

The nucleotide sequence of the genome of strain HC-J1 is shown in line (a) (SEQ ID NO:13) and that of strain HC-J4 in line (b) (SEQ ID NO:14), the latter showing only differing nucleotides vis a vis (a). Noncoding region nt1–324 is shown in small letters (SEQ ID NO: 1 for strain HC-J1 and SEQ ID NO: 15 for strain HC-J4). nt325–1863 (SEQ ID NO: 16 for strain HC-J1 and SEQ ID NO: 17 for strain HC-J4) is a region coding for various proteins starting with initiation codon ATG and is shown in capital letters (the nucleotide sequence in the aforementioned European Patent Application started only with the 1673th nucleotide, and missed the upstream sequence which is originally revealed in this invention):

```
(a) ggcgacactc caccatagat
(b) ---------- ----------
    cactcccctg tgaggaacta
    ---------- ----------
    ctgtcttcac gcagaaagcg
    ---------- ----------
    tctagccatg gcgttagtat
    ---------- ----------
    gagtgtcgtg cagcctccag   100
    ---------- ----------
    gacccccct cccgggagag
    ---------- ----------
    ccatagtggt ctgcggaacc
    ---------- ----------
    ggtgagtaca ccggaattgc
    ---------- ----------
    caggacgacc gggtcctttc
    ---------- ----------
    ttggataaac ccgctcaatg   200
    ------c--- ----------
    cctggagatt tgggcgcgcc
    ---------- ------t---
    cccgcaagac tgctagccga
    -----g---- ----------
```

-continued
```
gtagtgttgg gtcgcgaaag
---------- ---------- gccttgtggt actgcctgat
---------- ---------- agggtgcttg cgagtgcccc 300
---------- ---------- gggaggtctc gtagaccgtg
---------- ---------- caccATGAGC ACGATTCCCA
---------- ----A---T-

AACCTCAAAG AAAAACCAAA
---------- ----------

CGTAACACCA ACCGTCGCCC
---------- ----C-----

ACAGGACGTC AAGTTCCCGG 400
---------- ----------

GTGGCGGTCA GATCGTTGGT
-C--T----- ----------

GGAGTTTACT TGTTGCCGCG
---------C ----------

CAGGGGCCCT AGATTGGGTG
---------C --C-------

TGCGCGCGAC GAGGAAGACT
---------- T---------

TCCGAGCGGT CGCAACCTCG 500
---------- ----------

AGGTAGACGT CAGCCTATCC
T--AT-G--A --A-------

CCAAGGTGCG TCGGCCCGAG
------CT-- C--A------

GGCAGGACCT GGGCTCAGCC
------G--- ----------

CGGGTACCCT TGGCCCCTCT
---------- ----------

ATGGCAATGA GGGCTGCGGG 600
---------- -----TG---

TGGGCGGGAT GGCTCCTGTC
-----A---- ----------

TCCCCGTGGC TCTCGGCCTA
A-----C--- --C-------

GTTGGGGCCC CACGGACCCC
---------- ----------

CGGCGTAGGT CGCGCAATTT
---------- ----T--C--
```

-continued
```
GGGTAAGGTC ATCGATACCC 700
---------- ----------

TCACGTGCGG CTTCGCCGAC
-T--A----- ---------T

CTCATGGGGT ACATACCGCT
---------- -T--T-----

CGTCGGCGCC CCTCTTGGAG
---------- --C--A--G-

GCGCTGCCAG GGCCCTGGCG
---------- ----T----A

CATGGCGTCC GGGTTCTGGA 800
--C--T---- ----------

AGACGGCGTG AACTATGCAA
G--------- ----------

CAGGGAACCT TCCTGGTTGC
--------T- G--C------

TCTTTCTCTA TCTTCCTTCT
---------- -------CT-

GGCCCTGCTC TCTTGCCTGA
---TT----G --C--TT---

CTGTGCCCGC TTCAGCCTAC 900
-CA-C--A-- ---C--T--T

CAAGTGCGCA ACTCCACAGG
G--------- --GTGT-C--

GCTTTATCAT GTCACCAATG
-A-A--C--- -----G--C-

ATTGCCCTAA CTCGAGTATT
-C---T-C-- ---A--C---

GTGTACGAGG CGCACGATGC
-----T---- -------CAT

CATCCTGCAT ACTCCGGGGT 1000
G---A----- -----C----

GTGTCCCTTG CGTTCGCGAG
-C--G--C-- ------G---

GGCAACGTCT CGAGGTGTTG
-A----AG-- -CC-T--C--

GGTGGCGATC ACCCCCACGG
---A---C-C --T------C

TAGCCACCAG GGACGGCAAA
-C--GG---- -A-T-C--GC

CTCCCCGCGA CGCAGCTTCG 1100
G-----A-T- --ACAA-A--

ACGTCACATC GATCTGCTTG
---C---G-- --CT----C-
```

```
-continued
TCGGGAGCGC CACCCTCTGT
-T---GCG-- TG-TT----C
TCGGCCCTCT ACGTGGGGGA
--C--TA-G- ----------
TCTGTGCGGG TCCGTCTTCC
---C-----A --T--T----
TTATTGGTCA ACTGTTTACC 1200
-CG-CTCC-- G-----C---
TTCTCTCCCA GGCGCCACTG
-----G--TC -C--G--TGA
GACAACGCAA GGCTGCAATT
----GT---G -A------C-
GTTCTATCTA CCCCGGCCAT
-C--A----- T---------
ATAACGGGTC ATCGCATGGC
T--T-A---- -C--------
ATGGGATATG ATGATGAACT 1300
T--------- ----------
GGTCCCCTAC GGCGGCGTTG
----A----- AA-A--CC-A
GTAATGGCTC AGCTGCTCCG
--GG--T-G- --T-------
GATCCCACAA GCCATCTTGG
---------- --TG--G---
ATATGATCGC TGGTGCTCAC
-C---G-G-- G--G--C---
TGGGGAGTCC TGGCGGGCAT 1400
---------- --------C-
AGCGTATTTC TCCATGGTGG
T--C--C-AT --------A-
GGAACTGGGC GAAGGTCCTG
---------- T---------
GTAGTGCTGT TGCTGTTTGC
A-T---GC-C -A--C--C--
CGGCGTCGAC GCGGAAACCA
------T--- -G---G---T
TCGTCTCCGG GGGACAAGCC 1500
A-ACG--G-- ---GGCG---
GCCCGCGCCA TGTCTGGACT
AG--A-A--- CC--CACG--
TGTTAGTCTC TTCACACCAG
C-CGTCC--- ---T----T-
GCGCTAAGCA GAACATCCAG
-G--GTCT-- --GA------
```

```
-continued
CTGATCAACA CCAACGGCAG
--TG-G--T- ----------
TTGGCACATC AATAGCACGG 1600
C--------- --C--G--T-
CCTTGAACTG CAATGAAAGC
--C-A----- ------CTC-
CTTAACACCG GCTGGTTAGC
--CC----T- -G-TCC-T--
AGGGCTTATC TATCAACACA
C-C---GT-- --CAC-----
AATTCAACTC TTCGGGCTGT
GG-------- G--C--G--C
CCCGAGAGGT TGGCCAGCTG 1700
--G---C-CA ----------
CCGACGCCTT ACCGATTTTG
---C-C-A-- GA-TGG--C-
ACCAGGGCTG GGGCCCTATC
C------A-- ------C---
AGTCATGCCA ACGGAAGCGG
-CCT--A-TG -GCCTGA-A-
CCCCGACCAA CGCCCTATT
---G--T--G A-G--T----
GTTGGCACTA CCCCCCAAAA 1800
-C-----T-- -G-G--TCG-
CCTTGCGGTA TCGTGCCCGC
--G--T---- ----A-----
AAAGAGCGTA TGTGGCCCGG
GTC-CAG--G -----T--A-
TATATTGCTT CACTCCCAGC
-G-------- ---C--A---
CCC 1868
--T
```

For the gene region (nt325–1863) of strains HC-J1 and HC-J4, the sequences of 513 amino acids encoded were determined and homology, amino acids components and hydrophilicity of the amino acids between the two strains were studied. As a result, region nt325–864 was considered to be coding for the NANB hepatitis virus core proteins. Mutations or differences in the nucleotide sequence in this region were relatively smaller than in other coding regions and approximately 80% of the nucleotide mutations or differences identified were not accompanied by a change in amino acid sequence. Together with the nucleotide sequence of the 5' noncoding region already described above, the sequences of the structural gene region were also helpful in choosing appropriate nucleotide sequences of oligonucleotide primers used for the detection system in this invention. The envelope proteins are considered to be encoded by nucleotides 865–1476 and nonstructural proteins encoded by nucleotides 1477 and above.

The inventors have also identified that among oligonucleotide primers for the core region, the primer #25 (nt807–826), which has the least mutations or differences, is the best for the detection system of this invention.

Example 2

Synthesis or primers and the establishment of the detection system based on the 5' noncoding region and the core protein coding region.

(1) Synthesis of oligonucleotide primers.

Oligonucleotide primers (20 mer) were synthesized based on the 5' noncoding region sequences and the core protein coding region of strains HC-J1 and HC-J4 determined in Example 1. Oligonucleotide primer of HCV was also synthesized according to the nucleotide sequence disclosed in the European Patent Application No. 88310922.5 previously described. The model 3808 DNA Synthesizer (Applied Biosystems Japan) was used for such synthesis.

The number of primers synthesized were 20 (#3, 4, 5, 6, 9, 10, 11, 12, 16, 17, 21, 22, 23, 25, 32, 33, 34, 35, 36 and 48), and the position from the 5' terminus and nucleotide sequence for each of them is shown in Table 1.

(2) Isolation of NANB hepatitis viral RNA from a sample.

1 ml of a plasma sample was centrifuged on a model TL-100 (Beckman) ultracentrifuge at $9 \times 10^4$ rpm for 15 minutes and the precipitate thus obtained was suspended in buffer (containing 200 mM NaCl, 10 mM EDTA, 2% (w/v) sodium dodecyl sulfate (SDS) and proteinase K (1 mg/ml)) for incubation at 60° C. for 1 hour.

Nucleic acids were extracted twice by using the same volume of phenol/chloroform and precipitated in ethanol at −20° C. for over 3 hours. The precipitate was suspended in 70% ethanol for centrifugation and the precipitate was dissolved in 5 μl of distilled water after lyophilization.

(3) cDNA synthesis.

RNA extracted from a plasma sample in (2) above was denatured by heating at 70° C. for 1 minute and cooled on ice before synthesis of cDNA. cDNA was synthesized by reverse transcription. 100 pmol each of antisense primers #5, 6, 11, 12, 16, 17, 25, 35, 36 and 48 were added with 4 kinds of deoxyribonucleoside 5'-triphosphates (Takara, Japan), 10 units of RNase Inhibitor (Takara, Japan) and 10 units of Reverse transcriptase AMV (Boehringer Mannheim, Germany), and incubated at 42° C. for 90 minutes in a buffer (containing 10 μl of Tris chloride (50 mM, pH 8.4), 8 mM $MgCl_2$, 30 mM KCl and 1 mM dithiothreitol) to synthesize cDNA. cDNA thus obtained was purified by phenol/chloroform extraction.

(4) Amplification by PCR.

PCR was carried out using DNA Thermal Cycler (Perkin-Elmer Cetus) and DNA Amplification Reagent Kit (Perkin-Elmer Cetus) by the well-known method of Saiki et al. (1988). The reaction cycle of denaturalization (one minute at 94° C.), annealing of primers (1.5 minutes at 55° C.), and amplification of primers (3 minutes at 72° C.) was repeated 35 times.

The PCR product was electrophoresed in a mixed agarose gel of 1–1.5% Nusieve and 1–1.5% Seakem (FMC), and, after staining with ethidium bromide, its bands were confirmed by ultraviolet radiation.

(5) Amplification by second-stage PCR.

The product obtained by the first pair of primers (#32 and #36, for example) by PCR can be subjected to second-stage PCR if necessary. As primers for such PCR, a pair of primers of nucleotides for regions within those of the first pair of primers (#33 and #48, for example) were chosen and PCR reaction cycle was repeated 30 times for 5 μl of the product obtained in the first-stage PCR. Reaction conditions for each cycle was denaturalization (1 minute at 94° C.), annealing (1.5 minutes at 55° C.), and amplification (2 minutes at 72° C.). The product obtained in the second-stage PCR was electrophoresed and analyzed in the method described in (4) above.

Example 3

Selection of pairs of primers effective for detection of NANB hepatitis virus by PCR.

Results of PCR tests with two pairs of primers for 10 samples determined positive for HCV antibody (plasma samples nos. 1, 3, 5, 7 and 9 from Japanese blood donors and serum samples nos. 2, 4, 6, 8 and 10 from NANB hepatitis patients) are shown in Table 2.

PCR amplification was tried for 10 target nucleotide sequence regions; 2 regions each from NS5, NS3, and E-NS1 and its upstream (NS=nonstructural region, E-NS1= nucleotide region bridging the envelope region and nonstructural region number 1) referred to in Chiron's European Application), 2 regions each from the core region and 5' noncoding region identified under this invention.

As a result, when two pairs of primers from the 5' noncoding region (#32/#36 and #33/#48) and one pair of primers from the core region (#23/#25) were used, expected sizes of NANB cDNA bands (242 bp, 145 bp and 377 bp) for respective regions were detected.

In the other 7 regions, however, only 2 to 9 out of 10 samples could successfully be amplified, although the presence of RNA itself was confirmed in each sample. It was therefore concluded that pairs of primers #32/#36 and #33/#48 from the 5' noncoding region, and #23/#25 from the core region, were widely effective for detection of HCV RNA. Thus, selection of primers from NS5, NS3 and E-NS1 regions coding for the nonstructural protein of the virus are quite insignificant.

In some cases, single-stage PCR is sufficient for detection of NANB hepatitis viral RNA. However, to enhance sensitivity, two-stage PCR is recommended.

For example, samples which did not show the expected band of 242 bp when their cDNA was synthesized using #36 primer and amplified by PCR with primers #36 and #32 (first-stage PCR) were then subjected to the second-stage PCR using primers #33 and #48 and the first-stage PCR product as a template (second-stage PCR). If the 145 bp band does not occur after second-stage PCR then the sample did not contain viral RNA.

Example 4

32 samples from chronic NANB hepatitis patients, 10 samples from chronic hepatitis B patients, and 12 samples from blood donors with normal ALT levels were tested for NANB hepatitis virus RNA by PCR. Results are shown in Table 3.

Preliminary test of 32 samples from NANB hepatitis patients showed 20 samples positive and 12 samples negative for anti-HCV. All 10 samples from hepatitis B patients and 12 samples from blood donors with normal ALT levels were negative for anti-HCV.

For the 20 samples out of the 32 total samples from NANB hepatitis patients which tested positive for anti-HCV, RNA was detected in 15 samples by the first-stage PCR and the remaining 5 by the second-stage PCR. Thus 100% of the samples (which tested positive for anti-HCV) tested positive by PCR.

Out of the 12 samples from NANB hepatitis patients which tested negative for anti-HCV, 7 samples by the first-stage PCR and 4 samples by the second-stage PCR (or 92%) turned out to be positive for NANB hepatitis viral RNA. All 10 hepatitis B cases and all 12 blood donor cases with normal ALT levels subjected to the test (so far as the second-stage PCR) were negative for the viral RNa. From these data, NANB hepatitis RNA detection system using oligonucleotide as primers has proven its excellent performance, and its two-stage PCR system in particular has proven its superb performance both in sensitivity (more than 50% higher than anti-HCV and detecting as much as 96.9% of NANB hepatitis viral RNA) and specificity.

(5) Sensitivity of the detection system for NANB hepatitis virus by cDNA/two-stage PCR.

Sensitivity of NANB hepatitis virus detection system by cDNA/two-stage PCR under this invention is described below. Results are shown in Table 4.

10-fold serially diluted samples of plasma (having known infectious unit of $10^7$ CID/ml) were prepared and tested 3 times. In the first-stage PCR, the expected band of 242 bp was confirmed for 100 CID/ml in two tests and as low as 10 CID/ml in the remaining one test.

In the second-stage PCR, the expected band of 145 bp was confirmed for 10 CID/ml in two tests and as low as 1 CID/ml in one test. No band was detected for concentrations less than 1 CID/ml or for negative samples.

Average titer of NANB hepatitis patients is estimated to be $10^{2-4}$ and the described detection system is considered to give clinically significant sensitivity for diagnosis of NANB hepatitis patients.

The present invention thus provides a highly sensitive and specific detection system for NANB hepatitis virus. Accordingly, this invention will become instrumental in accurate diagnosis of hepatitis patients and screening of donor blood for prevention of posttransfusion hepatitis.

The present invention also concerns a nucleotide sequence of NANB which contains at least a portion of the bases 1–1863 described above. The sequence is constituted of a plurality of nucleotides and contains at least one primer as shown in table 1. In addition, the sequence is terminated at least at one end with a primer as shown in table 1.

The present invention further concerns a method of detecting non-A, non-B hepatitis virus comprising:

(1) synthesizing cDNA from viral RNA;

(2) amplifying said cDNA by PCR in a first stage to produce a product;

(3) amplifying the product by PCR in a second stage. The amplifying is carried out by using at least one oligonucleotide primer according to claim 8. The primer in step (1) may be a pair of primers and the primer in step (2) may be a pair of primers from a region within the pair of primers in step (1). The pair of primers in step (1) may be primers #32 and #48 in table 1 and the pair of primers in step (2) may be primers #33 and #48 in table 1. The pairs of primers may be selected from pairs of primers #32/#36, #33/#48, and #23/#25 in table 1.

The present invention also concerns diagnostic test kits for detecting NANB in biological samples, including for example blood and serum samples. The test kit includes (1) at least one primer derived from the nucleotide sequence disclosed above, (2) dATP, dTTP, dGTP, and dCTP; and (3) heat stable DNA polymerase. Kits suitable for diagnosis of NANB and containing the appropriate reagents are constructed by packaging the appropriate materials, including the primer in suitable containers, along with the remaining reagents and materials required, as well as a suitable set of instructions for conducting the test.

Further variations and modifications of the invention will become apparent to those skilled in the art from the foregoing and are intended to be encompassed by the claims appended hereto.

Japanese Patent Application No. Heisei 2 Nen 153402, filed on Jun. 12, 1990, is relied on and incorporated by reference.

TABLE 1

| Primers | Nucleotide Position | Nucleotide Sequences |
|---|---|---|
| #3 | 126–145 (SEQ. ID NO: 18) | AAACCTTGCGGTATTGTGCC |
| #4 | 153–172 (SEQ. ID NO: 19) | AGTGTGTGTGGTCCGGTATA |
| #5 | 268–287 (SEQ. ID NO: 30) | CGGTGGCCTGGTATTGTTAA |
| #6 | 303–322 (SEQ. ID NO: 21) | GAGTTCATCCAGGTACAACC |
| #9 | 6427–6446 (SEQ. ID NO: 22) | AGATGGCTTTGTACGACGTG |
| #10 | 6490–6509 (SEQ. ID NO: 23) | TCCAATACTCACCAGGACAG |
| #11 | 6761–3780 (SEQ. ID NO: 24) | CACAGCTAGTTGTCAGTACG |
| #12 | 6786–6805 (SEQ. ID NO: 25) | TTGATGTAGCAAGTGAGGGT |
| #16 | 4029–4048 (SEQ. ID NO: 26) | CTGGTGACAGCAGCTGTAAA |
| #17 | 4061–4080 (SEQ. ID NO: 27) | TGAAGAGGAGGGTTTGGCTA |
| #21 | 3669–3688 (SEQ. ID NO: 28) | TATTGCCTGTCAACAGGCTG |
| #22 | 3759–3778 (SEQ. ID NO: 29) | CGAGAGTTCGATGAGATGGA |
| #23 | 450–469 (SEQ. ID NO: 3) | TAGATTGGGTGTGCGCGCGA |
| #25 | 807–826 (SEQ. ID NO: 4) | TCCCTGTTGCATAGTTCACG |
| #32 | 7–26 (SEQ. ID NO: 5) | ACTCCACCATAGATCACTCC |
| #33 | 46–65 (SEQ. ID NO: 6) | TTCACGCAGAAAGCGTCTAG |
| #34 | 475–494 (SEQ. ID NO: 30) | AAGACTTCCGAGCGGTCGCA |
| #35 | 568–587 (SEQ. ID NO: 31) | TTGCCATAGAGGGGCCAAGG |
| #36 | 229–248 (SEQ. ID NO: 7) | AACACTACTCGGCTAGCAGT |
| #48 | 171–190 (SEQ. ID NO: 8) | GTTGATCCAAGAAAGGACCC |

TABLE 2

Detection of NANB hepatitis viral RNA in HCV antibody positive samples by PCR using various sets of primers.

| | Primers | | | | | | | | | |
|---|---|---|---|---|---|---|---|---|---|---|
| | 5' noncoding Region | | presumable core gene | | E-NS1 | | NS3 | | NS5 | |
| Sample No. | #32 /#36 (242bp) | #33 /#48 (145bp) | #23 /#25 (377bp) | #34 /#35 (113bp) | #3 /#6 (197bp) | #4 /#5 (135bp) | #21 /#17 (412bp) | #22 /#16 (290bp) | #9 /#12 (379bp) | #10 /#11 (291bp) |
| 1 | + | + | + | + | + | + | + | + | + | + |
| 2 | + | + | + | + | − | + | + | + | + | − |
| 3 | + | + | + | + | − | + | + | + | + | − |
| 4 | + | + | + | + | − | + | − | + | + | − |
| 5 | + | + | + | + | − | − | − | + | + | − |
| 6 | + | + | + | + | − | + | + | + | + | − |
| 7 | + | + | + | + | − | − | − | + | + | − |
| 8 | + | + | + | + | − | − | − | + | + | − |
| 9 | + | + | + | − | − | + | − | − | − | − |
| 10 | + | + | + | − | − | + | − | − | − | − |

Samples Nos. 1,3,5,7 and 9 are taken from blood donors, and samples Nos. 2,4,6,8 and 10 are taken from chronic NANB hepatitis patients.

TABLE 3

NANB hepatitis viral RNA detection by cDNA two-stage PCR. One pair each of primers #32 and 36, and #33 and #48 was used for the first-stage and second-stage PCR respectively.

| Source of Samples | Total number of Samples | Number of samples positive for anti-HCV by ORTHO's EIA | Number of samples positive for NANB hepatitis viral RNA | | |
|---|---|---|---|---|---|
| | | | 1st-stage PCR | 2nd-stage PCR | Total (%) |
| Chronic NANB hepatitis | 32 | 20 (62.5%) | 22 | 9 | 31 (96.9%) |
| Chronic hepatitis B | 10 | 0 (0) | 0 | 0 | 0 (0) |
| Blood donors with normal ALT level | 12 | 0 (0) | 0 | 0 | 0 (0) |

TABLE 4

Detection of NANB hepatitis viral RNA by two-stage PCR in samples with known infectivity titers. One pair each of primers #32 and #36, and #33 and #48 were used for the first-stage and second-stage respectively.

| | | *Serial Dilution (CID/ml) | | | | | | | |
|---|---|---|---|---|---|---|---|---|---|
| Test | PCR | × $10^2$ ($10^5$) | × $10^3$ ($10^4$) | × $10^4$ ($10^3$) | × $10^5$ ($10^2$) | × $10^6$ (10) | × $10^7$ 1 | × $10^8$ 0.1 | Control (Negative) |
| First Test | 1st-stage | +++ | +++ | ++ | + | − | − | − | − |
| | 2nd stage | NT | NT | NT | + | + | − | − | − |
| Second Test | 1st-stage | +++ | +++ | ++ | + | +/− | − | − | − |
| | 2nd-stage | NT | NT | NT | + | + | + | − | − |
| Third Test | 1st-stage | +++ | +++ | ++ | + | − | − | − | − |
| | 2nd-stage | NT | NT | NT | + | + | − | − | − |

*Same plasma negative for HCV antibody and HCV RNA was used as diluent and Control. CID means Chimpanzee Infectious Dose.

What is claimed:

1. An isolated nucleotide sequence of non-A, non-B hepatitis virus consisting of SEQ ID NO: 13.

2. An isolated nucleotide sequence of non-A, non-B hepatitis virus consisting of nucleotides 1–1672 (SEQ ID NO:32) of the nucleotide sequence of claim 1.

3. An isolated nucleotide sequence of non-A, non-B hepatitis virus consisting of nucleotides 1–324 (SEQ ID NO:1) of the nucleotide sequence of claim 1.

4. An isolated nucleotide sequence of non-A, non-B hepatitis virus consisting of nucleotides 325–1863 (SEQ ID NO:16) of the nucleotide sequence of claim 1.

5. An isolated nucleotide sequence of non-A, non-B hepatitis virus consisting of nucleotides 325–864 (SEQ ID NO:33) of the nucleotide sequence of claim 1.

6. An isolated nucleotide sequence of non-A, non-B hepatitis virus consisting of nucleotides 865–1476 (SEQ ID NO:34) of the nucleotide sequence of claim 1.

7. An oligonucleotide primer derived from the nucleotide sequence of non-A, non-B hepatitis virus according to claim 2.

8. An oligonucleotide primer derived from the nucleotide sequence of non-A, non-B hepatitis virus according to claim 3.

9. An oligonucleotide primer derived from the nucleotide sequence of non-A, non-B hepatitis virus according to claim 5.

10. An oligonucleotide primer derived from the nucleotide sequence of non-A, non-B hepatitis virus according to claim 6.

11. The oligonucleotide primer according to claim 7, wherein said primer contains from 15 to 25 nucleotides.

12. The oligonucleotide primer according to claim 7, wherein said primer consists of primer #23 (SEQ ID NO: 3) in table 1.

13. The oligonucleotide primer according to claim 7, wherein said primer consists of primer #25 (SEQ ID NO: 4) in table 1.

14. The oligonucleotide primer according to claim 7, wherein said primer consists of primer #32 (SEQ ID NO: 5) in table 1.

15. The oligonucleotide primer according to claim 7, wherein said primer consists of primer #33 (SEQ ID NO: 6) in table 1.

16. The oligonucleotide primer according to claim 7, wherein said primer consists of primer #36 (SEQ ID NO: 7) in table 1.

17. The oligonucleotide primer according to claim 7, wherein said primer consists of primer #48 (SEQ ID NO: 8) in table 1.

18. The oligonucleotide primer according to claim 11, wherein said primer contains 20 nucleotides.

19. An isolated nucleotide sequence of non-A, non-B hepatitis virus consisting of SEQ ID NO: 15.

20. An isolated nucleotide sequence of non-A, non-B hepatitis virus consisting of at least a portion of SEQ ID NO: 13, said sequence being constituted of a plurality of nucleotides and containing at least one primer as shown in table 1.

21. An isolated nucleotide sequence of non-A, non-B hepatitis virus consisting of at least a portion of SEQ ID NO: 13, said sequence being constituted of a plurality of nucleotides and terminated at least at one end with a primer as shown in table 1.

* * * * *